US006713045B1

(12) United States Patent
Meade et al.

(10) Patent No.: US 6,713,045 B1
(45) Date of Patent: *Mar. 30, 2004

(54) TARGETED MAGNETIC RESONANCE IMAGING AGENTS FOR THE DETECTION OF PHYSIOLOGICAL PROCESSES

(75) Inventors: Thomas Meade, Wilmette, IL (US); Scott Fraser, La Canada, CA (US); Russell Jacobs, Pasadena, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 143 days.

This patent is subject to a terminal disclaimer.

(21) Appl. No.: 09/716,178

(22) Filed: Nov. 16, 2000

Related U.S. Application Data

(63) Continuation-in-part of application No. 09/405,046, filed on Sep. 27, 1999, which is a continuation-in-part of application No. 09/134,072, filed on Aug. 13, 1998, now Pat. No. 5,980,862, which is a continuation-in-part of application 08/971,855, filed on Nov. 17, 1997, now abandoned, which is a continuation-in-part of application No. 08/486,968, filed on Jun. 7, 1995, now Pat. No. 5,707,605, which is a continuation-in-part of application No. 08/460,511, filed on Jun. 2, 1995, now abandoned.

(60) Provisional application No. 60/207,619, filed on May 26, 2000, provisional application No. 60/202,108, filed on May 4, 2000, and provisional application No. 60/063,328, filed on Oct. 27, 1997.

(51) Int. Cl.[7] .............................. A61B 5/055
(52) U.S. Cl. ................. 424/9.35; 424/1.11; 424/1.65; 424/9.1; 424/9.3; 424/9.323
(58) Field of Search ................. 424/1.11, 1.65, 424/1.73, 9.1, 9.3, 9.32, 9.323, 9.34, 9.341, 9.5, 9.36, 9.361, 9.7; 534/7, 10–16

(56) References Cited

U.S. PATENT DOCUMENTS

| | | | |
|---|---|---|---|
| 3,919,102 | A | 11/1975 | Kühling et al. |
| 4,647,447 | A | 3/1987 | Gries |
| 4,678,667 | A | 7/1987 | Meares et al. |
| 4,822,594 | A | 4/1989 | Gibby |
| 4,885,363 | A | 12/1989 | Tweedle et al. |
| 5,087,440 | A | 2/1992 | Cacheris et al. |
| 5,133,956 | A | 7/1992 | Garlich et al. |
| 5,155,215 | A | 10/1992 | Ranney |
| 5,188,816 | A | 2/1993 | Sherry et al. |
| 5,219,553 | A | 6/1993 | Kraft et al. |
| 5,256,395 | A | 10/1993 | Barbet et al. |
| 5,262,532 | A | 11/1993 | Tweedle et al. |
| 5,322,681 | A | 6/1994 | Klaveness |
| 5,332,567 | A | 7/1994 | Goldenberg |
| 5,358,704 | A | 10/1994 | Desreux et al. |
| 5,407,657 | A | 4/1995 | Unger et al. |
| 5,419,893 | A | 5/1995 | Berg et al. |
| 5,446,145 | A | 8/1995 | Love et al. |
| 5,466,439 | A | 11/1995 | Gibby et al. |
| 5,531,978 | A | 7/1996 | Berg et al. |
| 5,554,748 | A | 9/1996 | Sieving et al. |
| 5,565,552 | A | 10/1996 | Magda et al. |
| 5,707,605 | A | 1/1998 | Meade et al. |
| 5,914,095 | A | 6/1999 | Watson |
| 5,955,605 | A | 9/1999 | Axworthy et al. |
| 5,980,862 | A | 11/1999 | Meade et al. |

FOREIGN PATENT DOCUMENTS

| | | |
|---|---|---|
| CA | 2139374 A1 | 7/1995 |
| WO | WO 90/12050 A1 | 10/1990 |
| WO | WO 92/19264 A1 | 11/1992 |
| WO | WO 94/03271 | 2/1994 |
| WO | WO 94/04485 | 3/1994 |
| WO | WO 95/10217 | 4/1995 |
| WO | WO 95/19185 | 7/1995 |
| WO | WO 95/19347 | 7/1995 |
| WO | WO 95/20353 | 8/1995 |
| WO | WO 95/27705 A1 | 10/1995 |
| WO | WO 95/28966 A1 | 11/1995 |
| WO | WO 95/31444 A1 | 11/1995 |
| WO | WO 95/32741 A1 | 12/1995 |
| WO | WO 96/05167 A1 | 2/1996 |
| WO | WO 96/23526 A2 | 8/1996 |
| WO | WO 96/38184 A2 | 12/1996 |
| WO | WO 97/01360 | 1/1997 |
| WO | WO 97/21431 A1 | 6/1997 |
| WO | WO 97/32862 A1 | 9/1997 |
| WO | WO 97/36619 A2 | 10/1997 |
| WO | WO 99/21592 A1 | 5/1999 |
| WO | WO 99/25389 A2 | 5/1999 |
| WO | WO 99/59640 | 11/1999 |
| WO | WO 01/08712 A2 | 2/2001 |
| WO | WO 01/52906 A2 | 7/2001 |
| WO | WO 01/82795 A2 A3 | 11/2001 |

OTHER PUBLICATIONS

Aguayo, J.B., et al. "Nuclear Magnetic Resonance Imaging of a Single Cell," Nature, Letters to Nature 322:190–191 (Jul. 10, 1986).

Alexander, "Design and Synthesis of Macrocyclic Ligands and Their Complexes of Lanthanides and Antinides," Chem. Review, 95:273–342 (1995).

Borch, R.F., et al. "The Cyanohydridoborate Anion as a Selective Reducing Agents," Journal of the American Chemical Society 93 (12): 2897–2904 (Jun. 16, 1971).

Cho, Z.H., et al. "Some Experiences on a 4μμm NMR Microscopy," Book of Abstracts, vol. 1, p. 233, Society of Magnetic Resonance in Medicine, 6th Annual Meeting and Exhibition, Aug. 17–21, 1987, New York City, NY.

Grynkiewicz, G., et al. "A New Generation of Ca2+ Indicators with Greatly Improved Fluorescence Properties," The Journal of Biological Chemistry, 260(6): 3440–3450 (1985).

(List continued on next page.)

*Primary Examiner*—Dameron L. Jones
(74) *Attorney, Agent, or Firm*—Dorsey & Whitney LLP; Robin M. Silva; Renee M. Kosslak

(57) ABSTRACT

The invention relates to novel targeted magnetic resonance imaging contrast agents and methods of detecting physiological signals or substances.

18 Claims, 3 Drawing Sheets

OTHER PUBLICATIONS

Hennessy, M.J., et al. "NMR Surface Coil Microscopy," Book of Abstracts, vol. 2, p. 461–462, Society of Magnetic Resonance in Medicine, 5th Annual Meeting and Exhibition, Aug. 19–22, 1986, Montreal, Quebec, Canada.

Hoult, D.I., et al. "The Signal–to–Noise Ratio of the Nuclear Magnetic Resonance Experiment," Journal of Magnetic Resonance, 24: 71–85 (1976).

Jackels, "Section III: Enhancement Agents for Magnetic Resonance and Ultrasound Imaging. Chapter 20: Enhancement Agents for Magnetic Resonance Imaging: Fundamentals," Pharm. Med. Imag. Section III, Chap. 20, pp. 645–661 (1990).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. p. 23.

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moi, M.K., et al. "The Peptide Way to Macrocyclic Bifunctional Chelating Agents: Synthesis of 2–(p–Nitrobenzyl) –1,4,7,10–tetraazacyclododecan– N, N", N", N–tetraacetic Acid and Study of Its Yttrium (III) Complex," J. Am. Chem. Soc. 110(18):6266–6267 (1988).

Nijhof, E.J., et al."High–Resolution Proton Imaging at 4.7 Tesla," Proceedings of Soc. Magn. Reson. Med., p. 925 (1987).

Runge, V.M., et al. "Future Directions in Magnetic Resonance Contrast Media," Top Magn. Reson. Imaging., 3(2):85–97 (1991).

Russell, E.J., et al. "Multicenter Double–Blind Placebo–Controlled Study of Gadopentetate Dimeglumine as an MR Contrast Agent: Evaluation in Patients with Cerebral Lesions," American Journal of Roentgenology, 152:813–823 (Apr. 1989).

Sillerud, L.O., et al. "Proton NMR Microscopy of Intact Multicellular Tumor Spheroids," Book of Abstracts, vol. 1, p. 468, Society of Magnetic Resonance in Medicine, 6th Annual Meeting and Exhibition, Aug. 17–21, 1987, New York City, NY.

Tsien, R.Y. "New Calcium Indicators and Buffers with High Selectivity Against Magnesium and Protons: Design, Synthesis, and Properties of Prototype Structures," Biochemistry, 19(11): 2396–2404 (1980).

Tweedle, M.F., et al. "Considerations Involving Paramagnetic Coordination Compounds as Useful NMR Contrast Agents," Nucl. Med. Bio. 15(1):31–36 (1988).

Hubin et al., "Ultra rigid cross–bridged tetraazamacrocyles as ligands– the challenge and the solution," Chem. Commun., 1675–1676 (1998).

Hubin et al., "Crystallographic Characterization of Stepwise Changes in LIgand Conformations as Their Internal Topology changes and Two Novel Cross–Bridged Tetraazamacrocylic Copper (II) Complexes," Inorg. Chem. 38:4435–4446 (1999).

Hubin et al., "New Iron (II) and Manganese (II) Compleses of Two Ultra–Rigid, Cross–Briged Tetraazamacrocyles for Catalysis and Biomimicry," J. Am. Chem. Soc. 122:2515–2522 (2000).

Hubin et al., "Potentiometric Titrations and Nickel (II) Complexes of Four Topologically Constrained Tetraazamacrocycles," Supramolecular Chemistry, 13:261–276 (2001).

Weisman et al., "Cross–Bridged Cyclam. Protonation and $Li^+$Complexation in a Diamond–Lattice Cleft," J. Am. Chem. Soc. 112:8604–8605 (1990).

Weisman et al., "Synthesis and tranxition–metal complexes of new cross–bridged tetraamine ligands," Chem. Commun., 947–948 (1996).

Wong et al., "Synthesis and Characterization of Cross–bridged Cyclams and Pendant–Armed Derivatives and Structural studies of their Copper(II) Complexes," J. Am. Chem. Soc. 122:10561–10572 (2000).

Li, et al., "A Calcium–Sensitive Magnetic Resonance Imaging Contrast Agent," J. Am. Chem. Soc., 121:1413–1414 (1999).

Moats, et al., "A 'Smart' Magnetic Resonance Imaging Agent That Reports on Specific Enzymatic Activity," Angew. Chem. Int. Ed. Engl., 36(7): 726–728 (Apr. 1997).

Shukla, et al., "Design of Conformationally Rigid Dimeric MRI Agents," Magnetic Resonance in Medicine, 36(6): 928–931 (1996).

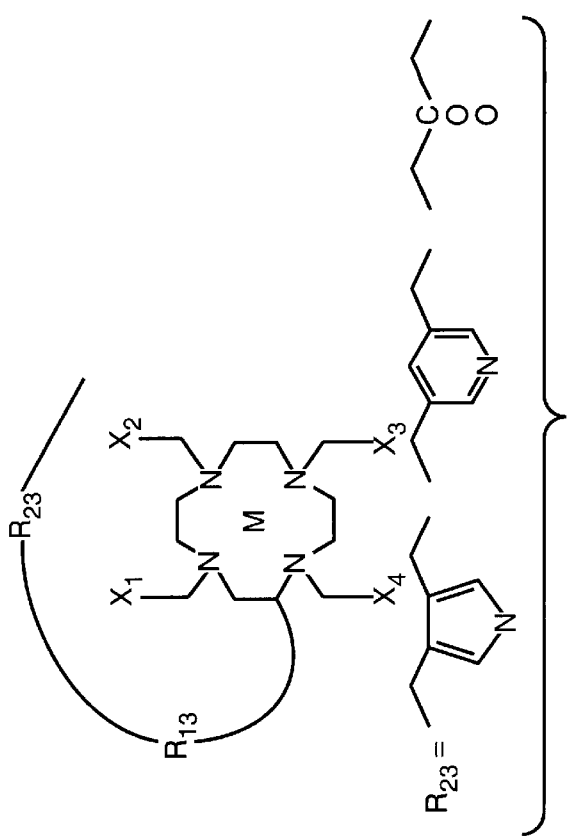
FIG._1
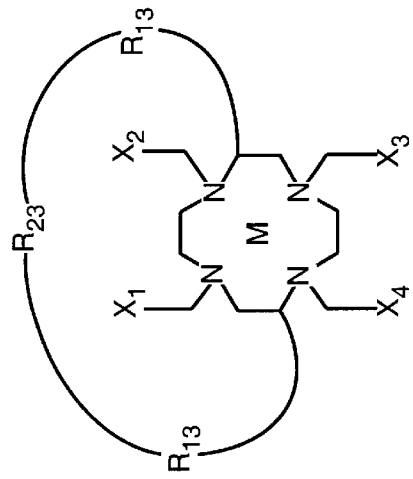
FIG._2
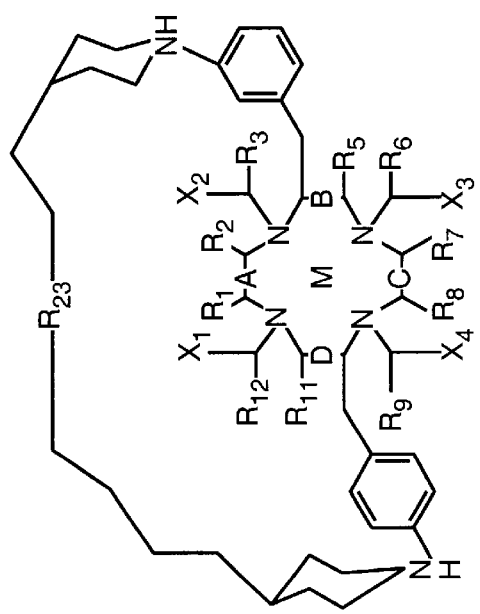
FIG._3
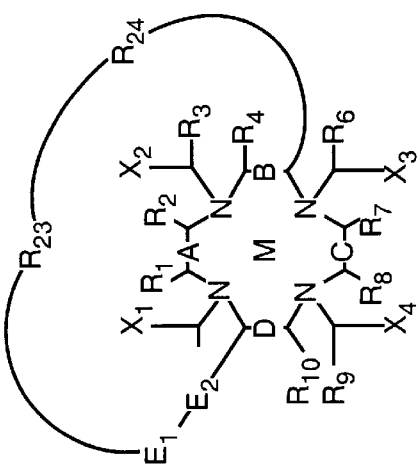
FIG._4

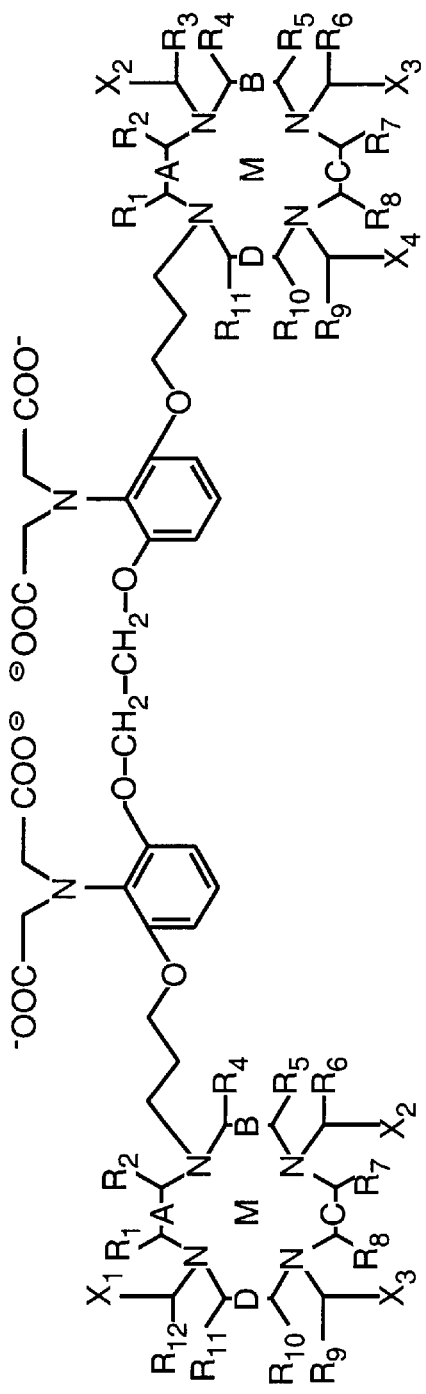
FIG._5
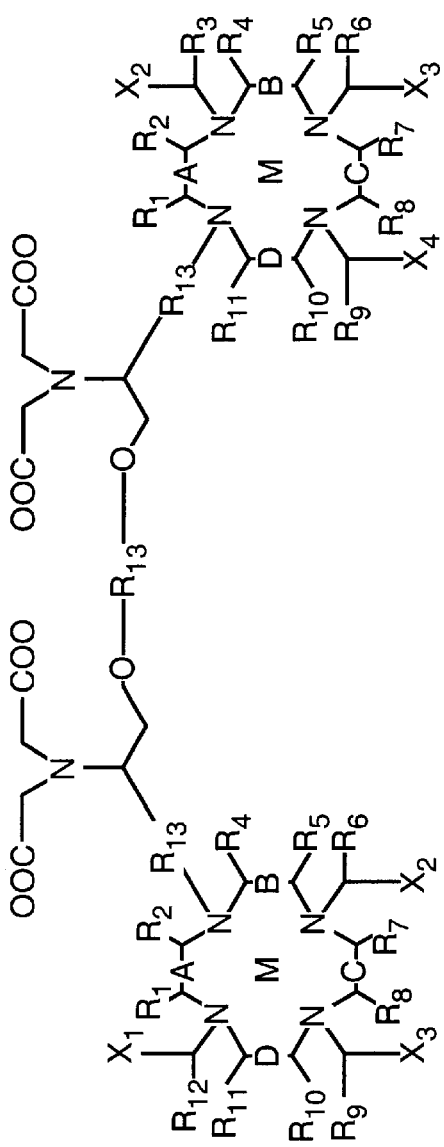
FIG._7

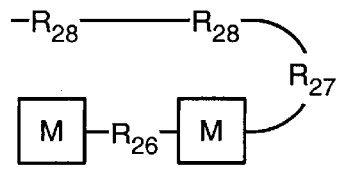
FIG._6A
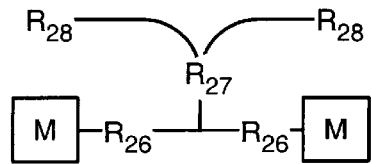
FIG._6B
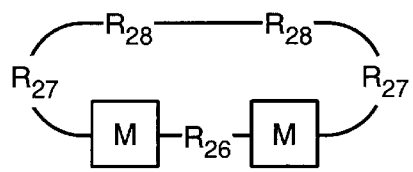
FIG._6C
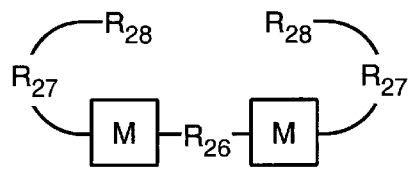
FIG._6D
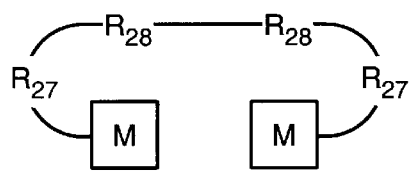
FIG._6E
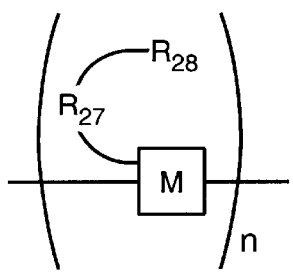
FIG._6F
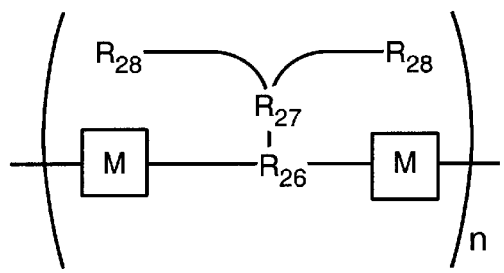
FIG._6G
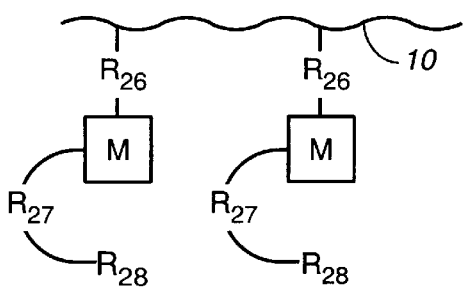
FIG._6H
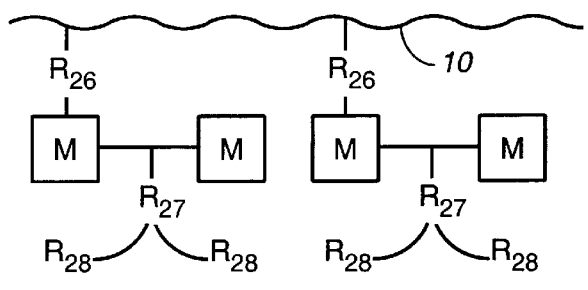
FIG._6I

TARGETED MAGNETIC RESONANCE IMAGING AGENTS FOR THE DETECTION OF PHYSIOLOGICAL PROCESSES

This application claims the benefit of the filing dates of U.S. Ser. No. 60/207,619, filed May 26, 2000, and No. 60/202,108, filed May 4, 2000,; and is a continuation-in-part of U.S. Ser. No. 09/405,046, filed Sep. 27, 1999, pending; which is a continuation-in-part of U.S. Ser. No. 09/134,072, filed Aug. 13, 1998, issued Nov. 9, 1999 as U.S. Pat. No. 5,980,862; which is a continuation-in-part of U.S. Ser. No. 08/971,855, filed Nov. 17, 1997, abandoned; which claims the benefit of the filing dates of U.S. Ser. No. 60/063,328, filed Oct. 27, 1997, and International Application Ser. No. US96/08548, filed Jun. 3, 1996, and is a continuation-in-part of U.S. Ser. No. 08/486,968, filed Jun. 7, 1995, issued Jan. 13, 1998 as U.S. Pat. No. 5,707,605; which is a continuation-in-part of U.S. Ser. No. 08/460,511, filed Jun. 2, 1995, abandoned; all of which are expressly incorporated by reference in their entirety.

FIELD OF THE INVENTION

The invention relates to novel targeting magnetic resonance imaging contrast agents and methods of detecting physiological signals or substances.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image

MR images are typically displayed on a gray scale with black the lowest and white the highest measured intensity (I). This measured intensity I=C*M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content). Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents. In the design of MRI agents, strict attention must be given to a variety of properties that will ultimately effect the physiological outcome apart from the ability to provide contrast enhancement. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($u^2$=63 $BM^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for $Gd(DTPA)^{2-}$ is very high (logK=22.4) and is more commonly known as the formation constant (the higher the logK, the more stable the complex). This thermodynamic parameter indicates the fraction of $Gd^{3+}$ ions that are in the unbound state will be quite small and should not be confused with the rate (kinetic stability) at which the loss of metal occurs ($k_f/k_d$). The water soluble $Gd(DTPA)^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N",N'''-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N"N'''-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

Previous work describes a new class of MRI contrast agents that report on physiologic or metabolic processes within a biological or other type of sample. See U.S. Pat. Nos. 5,707,605 and 5,980,862.

However, it would be desirable to target these functional MRI agents to tissues or locations to allow for better imaging. Accordingly, it is an object of the present invention to provide targeted MRI contrast or enhancement agents which allow the visualization and detection of physiological agents within an animal, tissue or cells.

SUMMARY OF THE INVENTION

In accordance with the above objects, the present invention provides MRI agent compositions comprising a first Gd(III) ion bound to a first chelator such that the Gd(III) ion has coordination atoms in at least 7 coordination sites of said Gd(III) ion and a first blocking moiety covalently attached to the first chelator which hinders the rapid exchange of water in the remaining coordination sites of the first Gd(III) ion. The blocking moiety is capable of interacting with a target substance such that the exchange of water in the remaining coordination sites of said first Gd(III) ion is increased. The agents further comprise at least a first targeting moiety. The agents optionally can comprise a second Gd(III) ion bound to a second chelator such that the second Gd(III) ion has coordination atoms in at least 7 coordination sites of the Gd(III) ion and a second blocking moiety covalently attached to the second chelator which hinders the rapid exchange of water in the remaining coordination sites of the second Gd(III) ion.

In an additional aspect, the invention provides MRI agents comprise chelators linked together using polymers.

In a further aspect, the invention provides MRI agents having the formula:

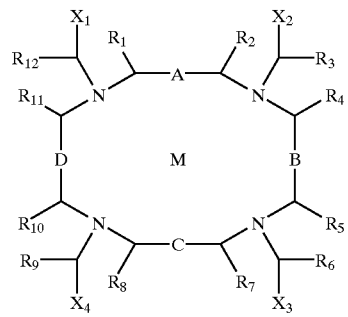

wherein
M is a paramagnetic metal ion selected from the group consisting of Gd(III), Fe(III), Mn(II), Yt(III), Cr(III) and Dy(III);
A, B, C and D are selected from the group consisting of single bonds or double bonds;
$X_1$, $X_2$, $X_3$ and $X_4$ are —OH, —COO—, —$CH_2OH$ —$CH_2COO$—, a blocking moiety or a targeting moiety;
$R_1$–$R_{12}$ are each a substitution group;
wherein at least one of $X_1$–$X_4$ and $R_1$–$R_{12}$ is a blocking moiety and wherein at least one of $X_1$–$X_4$ and $R_1$–$R_{12}$ is a targeting moiety.

In an additional aspect, the present invention provides MRI agent compositions having the formula:

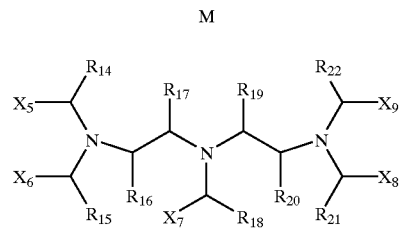

wherein
M is a paramagnetic metal ion selected from the group consisting of Gd(III), Fe(III), Mn(II), Yt(III), Cr(III) and Dy(III);
$X_5$, $X_6$, $X_7$, $X_8$ and $X_9$ are —OH, —COO—, —$CH_2OH$ —$CH_2COO$—, a blocking moiety or a targeting moiety;

$R_{14}$–$R_{22}$ are each a substitution group;

wherein at least one of $X_5$–$X_9$ and $R_{14}$–$R_{22}$ is a blocking moiety and wherein at least one of $X_5$–$X_9$ and $R_{14}$–$R_{22}$ is a targeting moiety.

In a further aspect, the invention provides pharmaceutical compositions comprising an MRI agent of the invention and a pharmaceutically acceptable carrier.

In an additional aspect, the present invention provides methods of magnetic resonance imaging of a cell, tissue or patient comprising administering an MRI agent of the invention to a cell, tissue or patient and rendering a magnetic resonance image of the cell, tissue or patient.

BRIEF DESCRIPTION OF THE DRAWINGS

FIG. 1 depicts a preferred embodiment. In this embodiment, the blocking moiety comprises two linkers, two carbohydrates, and a coordination site barrier. The carbohydrates are attached to the complex via a linkage which will be recognized by a carbohydrase such as a β(1, 4) linkage such as is recognized by lactose or β-galactosidase. The $R_{23}$ group provides a coordination atom in the absence of the carbohydrase such there is no rapid exchange of water in the complex. Upon exposure to the carbohydrase, such as β-galactosidase, one or both of the carbohydrate blocking moieties are cleaved off, removing the coordination atom and allowing the rapid exchange of water. Preferably, the R groups are hydrogen, and the X groups are carboxy. Alternatively, the blocking moiety could comprise peptides for a protease target substance. In addition, one of the $R_1$–$R_{12}$ and $X_1$–$X_4$ moieties comprises a targeting moiety.

FIG. 2 depicts an alternative embodiment. In this embodiment, there may not be covalent attachment at both ends. Rather, as discussed herein, effective "tethering" of the blocking moiety down over the metal ion may also be done by engineering in other non-covalent interactions that will serve to increase the affinity of the blocking moiety to the chelator complex. Thus, for example, electrostatic interactions may be used. The blocking moeity/coordination site barrier occupies the $X_3$ position, although any position may be utilized. $E_1$ and $E_2$ are electrostatic moieties bearing opposite charges. In this figure, the $E_2$ group is shown at position $R_8$, although any position may be used. In addition, one of the $R_1$–$R_{12}$ and $X_1$–$X_4$ moieties comprises a targeting moiety.

FIG. 3 depicts a representative complex of the invention, where the blocking moiety is tethered at one end only. As will be appreciated, the A, B, C and D bonds are depicted as single bonds, and there may be any number of additional R groups as outlined herein. The blocking moiety comprises a linker, $R_{13}$, which is preferably an enzyme substrate, and a coordination site barrier ($R_{23}$). In addition, one of the $R_1$–$R_{12}$ and $X_1$–$X_4$ moieties comprises a targeting moiety.

FIG. 4 depicts a representative complex of the invention, wherein the blocking moiety is tethered at two ends. In addition, one of the $R_1$–$R_{12}$ and $X_1$–$X_4$ moieties comprises a targeting moiety.

FIG. 5 depicts a preferred Ca+2 agent. As discussed herein, one of the $R_1$–$R_{12}$ and $X_1$–$X_4$ moieties comprises a targeting moiety; this can be on either chelate, or on both.

FIGS. 6A, 6B, 6C, 6D, 6E, 6F, and 6G depict several of the possible conformations of the dimer embodiments. Boxes represent chelators, with M being the paramagnetic metal ions. FIGS. 6A and 6B represent two possible duplex conformations. In FIG. 6A, $R_{27}$ can be a linker, such as described herein as $R_{26}$, a cleavable moiety such as an enzyme substrate such as a peptide, or a blocking moiety that will preferentially interact with the target molecule. $R_{28}$, which may or may not be present depending on $R_{27}$, is a coordination site barrier similar to $R_{23}$ or a blocking moiety. FIG. 6B has $R_{28}$ blocking moieties or coordination site barriers attached via an $R_{27}$ group to two chelators. FIG. 6C is similar to FIG. 6A, but at least one of the $R_{27}$ groups must be a cleavable moiety. FIG. 6D depicts the case where two blocking moieties or coordination site barriers are present; if $R_{27}$ is a blocking moiety, $R_{28}$ need not be present. FIG. 6E is similar to 6B but the chelators need not be covalently attached. FIGS. 6F (single MRI agents) and and 6G (duplex agents) are multimers of MRI contrast agents, wherein n can be from 1 to 1000, with from 1 to about 20 being preferred, and from about 1 to 10 being especially preferred. FIGS. 6H and 6I depict polymer 10 as defined herein being attached to either single MRI agents (6H) or duplex MRI agents (6I).

FIG. 7 depicts a preferred Ca+2 agent. As discussed herein, one of the $R_1$–$R_{12}$ and $X_1$–$X_4$ moieties comprises a targeting moiety; this can be on either chelate, or on both.

DETAILED DESCRIPTION OF THE INVENTION

The present invention provides novel targeted magnetic resonance imaging contrast agents which can detect physiological agents or target substances. Previous work has shown MRI contrast agents that are relatively inactive, or have weak relaxivity, as contrast enhancement agents in the absence of the physiological target substance, and are activated, thus altering the MR image, in the presence of the physiological target substance. See See U.S. Pat. Nos. 5,707,605 and 5,980,862; WO99/21592; and U.S. Ser. Nos. 09/405,046; 60/287,619; 60/203,224 and 60/201,816, all of which are expressly incorporated by reference.

Viewed simplistically, this "trigger" mechanism, whereby the contrast agent is "turned on" (i.e. increases the relaxivity) by the presence of the target substance, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the target substance in the surrounding environment. Thus, in the absence of the target substance, the metal ion complexes of the invention which chelate the paramagnetic ion have reduced coordination sites available which can rapidly exchange with the water molecules of the local environment. In such a situation, the water coordination sites are substantially occupied or blocked by the coordination atoms of the chelator and at least one blocking moiety. Thus, the paramagnetic ion has essentially no water molecules in its "inner-coordination sphere", i.e. actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are occupied with moieties other than water molecules, as is the case when the target substance is absent, there is little if any net enhancement of the imaging signal by the metal ion complexes of the invention. However, when present, the target substance interacts with the blocking moiety or moities of the metal ion complex, effectively freeing at least one of the inner-sphere coordination sites on the metal ion complex. The water molecules of the local environment are then available to occupy the inner-sphere coordination site or sites, which will cause an increase in the rate of exchange of water and relaxivity of the metal ion complex toward water thereby producing image enhancement which is a measure of the presence of the target substance.

It should be understood that even in the absence of the target substance, at any particular coordination site, there will be a dynamic equilibrium for one or more coordination sites as between a coordination atom of the blocking moiety and water molecules. That is, even when a coordination atom is tightly bound to the metal, there will be some exchange of water molecules at the site. However, in most instances, this exchange of water molecules is neither rapid nor significant, and does not result in significant image enhancement. However, upon exposure to the target substance, the blocking moiety dislodges from the coordination site and the exchange of water is increased, i.e. rapid exchange and therefore an increase in relaxivity may occur, with significant image enhancement.

Generally, a 2 to 5% change in the MRI signal used to generate the image is sufficient to be detectable. Thus, it is preferred that the agents of the invention in the presence of a target substance increase the MRI signal by at least 2 to 5% as compared to the signal gain the absence of the target substance. Signal enhancement of 2 to 90% is preferred, and 10 to 50% is more preferred for each coordination site made available by the target substance interaction with the blocking moiety. That is, when the blocking moiety occupies two or more coordination sites, the release of the blocking moiety can result in double the increase in signal or more as compared to a single coordination site.

The present invention is directed to the use of targeting moieties attached to these activatable MRI agents. By utilizing a targeting moiety, defined below, that can direct the MRI agent to a particular cell type, tissue, or location, the MRI agents of the invention become more effective, discriminatory and selective.

Accordingly, the complexes of the invention comprise a paramagnetic metal ion bound to a complex comprising a chelator and a blocking moiety. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator and a blocking moiety which may be covalently attached to the chelator. Due to the relatively high toxicity of many of the paramagnetic ions, the ions are rendered nontoxic in physiological systems by binding to a suitable chelator. Thus, the substitution of blocking moieties in coordination sites of the chelator, which in the presence of the target substance are capable of vacating the coordination sites in favor of water molecules, may render the metal ion complex more toxic by decreasing the half-life of dissociation for the metal ion complex. Thus, in a preferred embodiment, only a single coordination site is occupied or blocked by a blocking moeity. However, for some applications, e.g. analysis of tissue and the like, the toxicity of the metal ion complexes may not be of paramount importance. Similarly, some metal ion complexes are so stable that even the replacement of one or more additional coordination atoms with a blocking moiety does not significantly effect the half-life of dissociation. For example, DOTA, described below, when complexed with Gd(III) is extremely stable. Accordingly, when DOTA serves as the chelator, several of the coordination atoms of the chelator may be replaced with blocking moieties without a significant increase in toxicity. Additionally such an agent would potentially produce a larger signal since it has two or more coordination sites which are rapidly exchanging water with the bulk solvent.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion. The chelators used in the metal ion complexes of the present invention preferably have at least one less coordination atom (n-1) than the metal ion is capable of binding (n), since at least one coordination site of the metal ion complex is occupied or blocked by a blocking moiety, as described below, to confer functionality on the metal ion complex. Thus, for example, Gd(III) may have 8 strongly associated coordination atoms or ligands and is capable of weakly binding a ninth ligand. Accordingly, suitable chelators for Gd(III) will have less than 9 coordination atoms. In a preferred embodiment, a Gd(III) chelator will have 8 coordination atoms, with a blocking moiety either occupying or blocking the remaining site in the metal ion complex. In an alternative embodiment, the chelators used in the metal ion complexes of the invention have two less coordination atoms (n-2) than the metal ion is capable of binding (n), with these coordination sites occupied by one or more blocking moieties. Thus, alternative embodiments utilize Gd(III) chelators with at least 5 coordination atoms, with at least 6 coordination atoms being preferred, at least 7 being particularly preferred, and at least 8 being especially preferred, with the blocking moiety either occupying or blocking the remaining sites. It should be appreciated that the exact structure of the chelator and blocking moiety may be difficult to determine, and thus the exact number of coordination atoms may be unclear. For example, it is possible that the chelator provide a fractional or non-integer number of coordination atoms; i.e. the chelator may provide 7.5 coordination atoms, i.e. the 8th coordination atom is on average not fully bound to the metal ion. However, the metal ion complex may still be functional, if the 8th coordination atom is sufficiently bound to prevent the rapid exchange of water at the site, and/or the blocking moiety impedes the rapid exchange of water at the site.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorportated by reference. Thus, as will be understood by those in the art, any of the known paramagnetic metal ion chelators or lanthanide chelators can be easily modified using the teachings herein to further comprise at least one blocking moiety.

A preferred chelator, particularly when the metal ion is Gd(III), is 1,4,7,10-tetraazacyclododecane-N,N',N'',N'''-tetracetic acid (DOTA) or substituted DOTA. DOTA has the structure shown below:

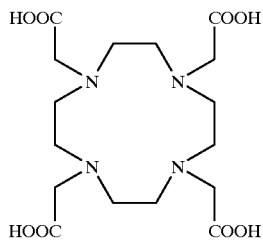

By "substituted DOTA" herein is meant that the DOTA may be substituted at any of the following positions, as shown below:

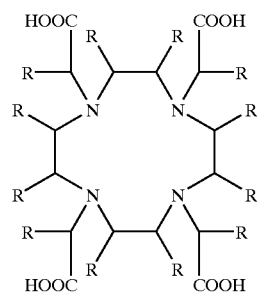

As will be appreciated by those in the art, a wide variety of possible R substituent groups may be used. Suitable R substitution groups, for this and other structures of the invention, include, but are not limited to, hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, cancer directed guarding moieties and targeting moieties. In addition, suitable substitution groups include substitution groups disclosed for DOTA and DOTA-type compounds in U.S. Pat. Nos. 5,262,532, 4,885,363, and 5,358,704 and WO 98/05625.

In addition, R groups on adjacent carbons, or adjacent R groups, can be attached to form cycloalkyl or cycloaryl groups, including heterocycloalkyl and heterocycloaryl groups together with the carbon atoms of the chelator, such as is described below and in U.S. Pat. No. 5,358,704, expressly incorporated by reference. These ring structures may be similarly substituted at any position with R groups.

In addition, as will be appreciated by those skilled in the art, each position designated above may have two R groups attached (R' and R''), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In a preferred embodiment, one R group is a blocking moiety and the other R groups are hydrogen; that is, it is preferred to have only two hydrogens at each R position except for the positions occupied by the blocking moiety and the targeting moiety. Similarly, preferred embodiments utilize one R group as a targeting moiety and the other R groups (except for the blocking moiety position) as hydrogen.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—$NH_2R$), secondary (—$NHR_2$), or tertiary (—$NR_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc. As for alkyl groups, the aryl group may be substituted with a substitution group, generally depicted herein as R.

By "amino groups" or grammatical equivalents herein is meant —$NH_2$ (amine groups), —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds (including sulfones ($SO_2$) and sulfides (SO)), thiols (—SH and —SR), and sulfides (—RSR—).

By "phosphorus containing moieties" herein is meant compounds containing phosphorus, including, but not limited to, phosphines, phosphites and phosphates. A preferred phosphorous moiety is the —PO(OH)(R)$_2$ group. The phosphorus may be an alkyl phosphorus; for example, DOTEP utilizes ethylphosphorus as a substitution group on DOTA. A preferred embodiment has a —PO(OH)$_2$R$_{25}$ group, with R$_{25}$ being a substitution group as outlined herein.

By "silicon containing moieties" herein is meant compounds containing silicon.

By "ketone" herein is meant an —RCOR— group.

By "aldehyde" herein is meant an —RCOH group.

By "ether" herein is meant an —R—O—R group.

By "alkyoxy group" herein is meant an —OR group.

By "ester" herein is meant a —COOR group.

By "halogen" herein is meant bromine, iodine, chlorine, or fluorine. Preferred substituted alkyls are partially or fully halogenated alkyls such as CF$_3$, etc.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—CH$_2$—CH$_2$)$_n$— group, although each carbon atom of the ethylene group may also be singly or doubly substituted, i.e. —(O—CR$_2$—CR$_2$)$_n$—, with R as described above. Ethylene glycol derivatives with other heteroatoms in place of oxygen (i.e. —(N—CH$_2$—CH$_2$)$_n$— or —(S—CH$_2$—CH$_2$)$_n$—, or with substitution groups) are also preferred.

Preferred substitution groups include, but are not limited to, alkyl, alkyoxy, amide, hydrogen, aryl and targeting moieties.

The substitution group may also be a targeting moiety or a blocking moiety, as is described below.

In an alternative embodiment, a preferred chelator, particularly when the metal ion is Gd(III), is diethylenetriaminepentaacetic acid (DTPA) or substituted DTPA. DPTA has the structure shown below:

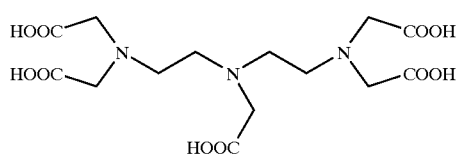

By "substituted DPTA" herein is meant that the DPTA may be substituted at any of the following positions, as shown below:

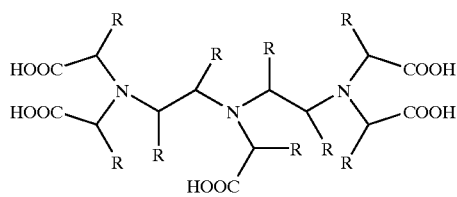

See for example U.S. Pat. No. 5,087,440.

Suitable R substitution groups include those outlined above for DOTA. Again, those skilled in the art will appreciate that there may be two R groups (R' and R") at each position designated above, although as described herein, at least one of the groups at each position is hydrogen, which is generally not depicted herein. In addition, adjacent R groups may be joined to form cycloalkyl or -aryl structures.

In an alternative embodiment, when the metal ion is Gd(III), a preferred chelator is 1,4,7,10-tetraazacyclododecane-N,N',N'',N'''-tetraethylphosphorus (DOTEP) or substituted DOTEP (see U.S. Pat. No. 5,188,816). DOTEP has the structure shown below:

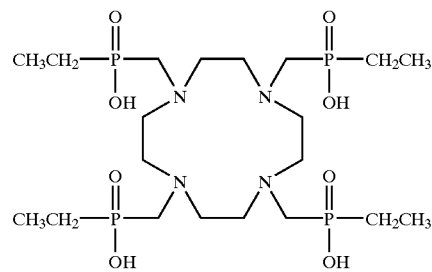

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); Carvavan, Chem. Rev. 99:2293–2352 (1999); Carvavan, Coord. Chem. Rev. 184:1–157 (1999); and U.S. Pat. Nos. 4,885,363, 5,358,704, and 5,262,532, all which describe chelators suitable for Fe(III).

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987);

Carvavan, Chem. Rev. 99:2293–2352 (1999); Carvavan, Coord. Chem. Rev. 184:1–157 (1999); and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since DyIII is capable of binding 8 or 9 coordination atoms. Suitable chelators are known in the art, as above.

In a preferred embodiment, as is further described below, the chelator and the blocking moiety are covalently linked; that is, the blocking moiety is a substitution group on the chelator. In this embodiment, the substituted chelator, with the bound metal ion, comprises the metal ion complex which in the absence of the target substance has all possible coordination sites occupied or blocked; i.e. it is coordinatively saturated.

In an alternative embodiment, the chelator and the blocking moiety are not covalently attached. In this embodiment, the blocking moiety has sufficient affinity for the metal ion to prevent the rapid exchange of water molecules in the absence of the target substance. However, in this embodiment the blocking moiety has a higher affinity for the target substance than for the metal ion. Accordingly, in the presence of the target substance, the blocking moiety will have a tendency to be dislodged from the metal ion to interact with the target substance, thus freeing up a coordination site in the metal ion complex and allowing the rapid exchange of water and an increase in relaxivity.

What is important is that the metal ion complex, comprising the metal ion, the chelator and the blocking moiety, is not readily able to rapidly exchange water molecules when the blocking moeities are in the inner coordination sphere of the metal ion, such that in the absence of the target substance, there is less or little substantial image enhancement.

In addition to the metal ions and chelators described herein, the MRI agents of the invention comprise a blocking moiety. By "blocking moiety" or grammatical equivalents herein is meant a functional group associated with the chelator metal ion complexes of the invention which is capable of interacting with a target substance and which is capable, under certain circumstances, of substantially blocking the exchange of water in at least one inner coordination site of the metal ion of the metal ion complex. For example, when bound to or associated with the metal ion complexes of the invention, the blocking moiety occupies or blocks at least one coordination site of the metal ion in the absence of the target substance. Thus, the metal ion is coordinately saturated with the chelator and the blocking moiety or moieties in the absence of the target substance.

A blocking moiety may comprise several components. The blocking moiety has a functional moiety which is capable of interacting with a target substance, as outlined below. This functional moiety may or may not provide the coordination atom(s) of the blocking moiety. In addition, blocking moieties may comprise one or more linker groups to allow for correct spacing and attachment of the components of the blocking moiety. Furthermore, in the embodiment where the functional group of the blocking moiety does not contribute a coordination atom, the blocking moiety may comprise a coordination site barrier, which serves to either provide a coordination site atom or sterically prevent the rapid exchange of water at the coordination site; i.e. the coordination site barrier may either occupy or block the coordination site.

By "capable of interacting with a target substance" herein is meant that the blocking moiety has an affinity for the target substance, such that the blocking moiety will stop blocking or occupying at least one coordination site of the metal ion complex when the target substance is present. Thus, as outlined above, the blocking moiety is blocking or occupying at least one coordination site of the metal ion in the absence of the target substance. However, in the presence of the target substance, the blocking moiety associates or interacts with the target substance and is released from its association with the metal ion, thus freeing at least one coordination site of the metal ion such that the rapid exchange of water can occur at this site, resulting in image enhancement.

The nature of the interaction between the blocking moiety and the target substance will depend on the target substance to be detected or visualized via MRI. For example, suitable target substances include, but are not limited to, enzymes; proteins; peptides; nucleic acids; ions such as $Ca^{+2}$, $Mg^{+2}$, $Zn^{+2}$, $K^+$, $Cl^-$, and $Na^+$; cAMP; receptors such as cell-surface receptors and ligands; hormones; antigens; antibodies; ATP; NADH; NADPH; $FADH_2$; $FNNH_2$; coenzyme A (acyl CoA and acetyl CoA); and biotin, among others.

In some embodiments, the nature of the interaction is irreversible, such that the blocking moiety does not reassociate to block or occupy the coordination site; for example, when the blocking moiety comprises an enzyme substrate which is cleaved upon exposure to the target enzyme. Alternatively, the nature of the interaction is reversible, such that the blocking moiety will reassociate with the complex to hinder the exchange of water; for example, when the blocking moiety comprises an ion ligand, or a receptor ligand, as outlined below.

The corresponding blocking moieties will be enzyme substrates or inhibitors, receptor ligands, antibodies, antigens, ion binding compounds, substantially complementary nucleic acids, nucleic acid binding proteins, etc.

In a preferred embodiment, the target substance is an enzyme, and the blocking moiety is an enzyme substrate. In this embodiment, the blocking moiety is cleaved from the metal ion complex of the invention, allowing the exchange of water in at least one coordination site of the metal ion complex. This embodiment allows the amplification of the image enhancement since a single molecule of the target substance is able to generate many activated metal ion complexes, i.e. metal ion complexes in which the blocking moiety is no longer occupying or blocking a coordination site of the metal ion.

As will be appreciated by those skilled in the art, the possible enzyme target substances are quite broad. The target substance enzyme may be chosen on the basis of a correlation to a disease condition, for example, for diagnositic purposes. Alternatively, the metal ion complexes of the present invention may be used to establish such correlations.

Suitable classes of enzymes include, but are not limited to, hydrolases such as proteases, carbohydrases, lipases and nucleases; isomerases such as racemases, epimerases, tautomerases, or mutases; transferases, kinases and phophatases.

As will be appreciated by those skilled in the art, the potential list of suitable enzyme targets is quite large. Enzymes associated with the generation or maintenance of arterioschlerotic plaques and lesions within the circulatory system, inflammation, wounds, immune response, tumors, may all be detected using the present invention. Enzymes such as lactase, maltase, sucrase or invertase, cellulase, α-amylase, aldolases, glycogen phosphorylase, kinases such as hexokinase, proteases such as serine, cysteine, aspartyl and metalloproteases may also be detected, including, but not limited to, trypsin, chymotrypsin, and other therapeutically relevant serine proteases such as tPA and the other proteases of the thrombolytic cascade; cysteine proteases including: the cathepsins, including cathepsin B, L, S, H, J, N and O; and calpain; and caspases, such as caspase-3, -5, -8 and other caspases of the apoptotic pathway, and interleukin-converting enzyme (ICE). Similarly, bacterial and viral infections may be detected via characteristic bacterial and viral enzymes. Particularly preferred are enzymes used as indicators of or treatment for: (1) heart disease, including creatine kinase, lactate dehydrogenase, aspartate amino transferase, troponin T, myoglobin, fibrinogen, cholesterol, triglycerides, thrombin, tissue plasminogen activator (tPA); (2) pancreatic disease indicators including amylase, lipase, chymotrypsin and trypsin; (3) liver function enzymes and proteins including cholinesterase, bilirubin, and alkaline phosphotase; aldolase, prostatic acid phosphatase, terminal deoxynucleotidyl transferase, and (4) bacterial and viral enzymes such as HIV protease. As will be appreciated in the art, this list is not meant to be limiting.

Once the target enzyme is identified or chosen, enzyme substrate blocking moieties can be designed using well known parameters of enzyme substrate specificities.

For example, when the enzyme target substance is a protease, the blocking moiety may be a peptide or polypeptide which is capable of being cleaved by the target protease. By "peptide" or "polypeptide" herein is meant a compound of about 2 to about 15 amino acid residues covalently linked by peptide bonds. Preferred embodiments utilize polypeptides from about 2 to about 8 amino acids, with about 2 to about 4 being the most preferred. Preferably, the amino acids are naturally occurring amino acids, although amino acid analogs and peptidomimitic structures are also useful, particularly in the design of inhibitors. Under certain circumstances, the peptide may be only a single amino acid residue.

Similarly, when the enzyme target substance is a carbohydrase, the blocking moiety will be a carbohydrate group which is capable of being cleaved by the target carbohydrase. For example, when the enzyme target is lactase or β-galactosidase, the enzyme substrate blocking moiety is lactose or galactose. Similar enzyme/blocking moiety pairs include sucrase/sucrose, maltase/maltose, and α-amylase/amylose.

In another embodiment, the blocking moiety may be an enzyme inhibitor, such that in the presence of the enzyme, the inhibitor blocking moiety disassociates from the metal ion complex to interact or bind to the enzyme, thus freeing an inner coordination sphere site of the metal ion for interaction with water. As above, the enzyme inhibitors are chosen on the basis of the enzyme target substance and the corresponding known characteristics of the enzyme.

In a preferred embodiment, the blocking moiety is a phosphorus moiety, as defined above, such as —(OPO(OR$_2$))$_n$, wherein n is an integer from 1 to about 10, with from 1 to 5 being preferred and 1 to 3 being particularly preferred. Each R is independently hydrogen or a substitution group as defined herein, with hydrogen being preferred. This embodiment is particularly useful when the target molecule is alkaline phosphatase or a phosphodiesterase, or other enzymes known to cleave phosphorus containing moieties such as these.

In one embodiment, the blocking moiety is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of electron transfer moieties, or to increase the stability and half-life of such molecules in physiological environments.

As will be appreciated by those in the art, all of these nucleic acid analogs may find use in the present invention. In addition, mixtures of naturally occurring nucleic acids and analogs can be made, or mixtures of different nucleic acid analogs, and mixtures of naturally occuring nucleic acids and analogs may be made.

Alternatively, as is generally described in U.S. Pat. Nos. 5,270,163, 5,475,096, 5,567,588, 5,595,877, 5,637,459, 5,683,867,5,705,337, and related patents, hereby incorporated by reference, nucleic acid "aptamers" can be developed for binding to virtually any target analyte; thus for example, aptamers may be developed to a wide variety of cancer moieties.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside. The target molecule can be a substantially complementary nucleic acid or a nucleic acid binding moiety, such as a protein.

In a preferred embodiment, the target substance is a physiological agent. As for the enzyme/substrate embodiment, the physiological agent interacts with the blocking moiety of the metal ion complex, such that in the presence of the physiological agent, there is rapid exchange of water in at least one inner sphere coordination site of the metal ion complex. Thus, the target substance may be a physiologically active ion, and the blocking moiety is an ion binding ligand. For example, as shown in the Examples, the target substance may be the Ca+2 ion, and the blocking moiety may be a calcium binding ligand such as is known in the art (see Grynkiewicz et al., J. Biol. Chem. 260(6):3440–3450 (1985); Haugland, R. P., Molecular Probes Handbook of Fluorescent Probes and Research Chemicals (1989–1991)). Other suitable target ions include Mn+2, Mg+2, Zn+2, Na+, and Cl−.

When Ca+2 is the target substance, preferred blocking moieties include, but are not limited to, the acetic acid groups of bis(o-amino-phenoxy)ethane-N,N,N',N'-tetraacetic acid (BAPTA), ethylene glycol bis(β-aminoethyl ether)-N,N,N',N'-tetraacetic acid (EGTA); ethylenediamine-tetracetic acid (EDTA); and derivatives thereof, such as disclosed in Tsien, Biochem. 19:2396–2404 (1980). Other known chelators of Ca+2 and other divalent ions, such as quin2 (2-[[2-[bis(carboxymethyl)amino]-5-methylphenoxy]methyl-6-methoxy-8-[bis(carboxymethyl)amino]quinoline; fura-1, fura-2, fura-3, stil-1, stil-2 and indo-1 (see Grynkiewicz et al., supra).

As for the enzyme/substrate embodiments, the metabolite may be associated with a particular disease or condition within an animal. For example, as outlined below, BAPTA-DOTA derivatives may be used to diagnose Alzeheimer's disease and other neurological disorders.

In a preferred embodiment, the blocking moiety is a ligand for a cell-surface receptor or is a ligand which has affinity for a extracellular component. In this embodiment, as for the physiological agent embodiment, the ligand has sufficient affinity for the metal ion to prevent the rapid exchange of water molecules in the absence of the target substance. Alternatively, there may be R groups "locking" the ligand into place, as described herein, resulting in either the contribution of a coordination atom or that the ligand serves as a coordination site barrier. In this embodiment the ligand blocking moiety has a higher affinity for the target substance than for the metal ion. Accordingly, in the presence of the target substance, the ligand blocking moiety will interact with the target substance, thus freeing up at least one coordination site in the metal ion complex and allowing the rapid exchange of water and an increase in relaxivity. Additionally, in this embodiment, this may result in the accumulation of the MRI agent at the location of the target, for example at the cell surface. This may be similar to the situation where the blocking moiety is an enzyme inhibitor, as well.

In this embodiment, the blocking moiety may be all or a portion (e.g. a binding portion) of a ligand for a cell surface receptor. Suitable ligands include, but are not limited to, all or a functional portion of the ligands that bind to a cell surface receptor selected from the group consisting of ligands that bind to: insulin receptor (insulin), insulin-like growth factor receptor (including both IGF-1 and IGF-2), growth hormone receptor, estrogen receptor; glucose transporters (particularly GLUT 4 receptor), transferrin receptor (transferrin), epidermal growth factor receptor (EGF), low density lipoprotein receptor, high density lipoprotein receptor, leptin receptor, interleukin receptors including IL-1, IL-2, IL-3, IL4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, corticotropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, glucocorticoids and the hormones above. Receptor ligands include ligands that bind to receptors such as cell surface receptors, which include hormones, lipids, proteins, glycoproteins, signal transducers, growth factors, cytokines, and others.

In a preferred embodiment, the blocking moiety is a photocleavable moiety. That is, upon exposure to a certain wavelength of light, the blocking moiety is cleaved, allowing an increase in the exchange rate of water in at least one coordination site of the complex. This embodiment has particular use in developmental biology fields (cell lineage, neuronal development, etc.), where the ability to follow the fates of particular cells is desirable. Suitable photocleavable moieties are similar to "caged" reagents which are cleaved upon exposure to light. A particularly preferred class of photocleavable moieties are the O-nitrobenzylic compounds, which can be synthetically incorporated into a blocking moiety via an ether, thioether, ester (including phosphate esters), amine or similar linkage to a heteroatom (particularly oxygen, nitrogen or sulfur). Also of use are benzoin-based photocleavable moieties. A wide variety of suitable photocleavable moieties is outlined in the Molecular Probes Catalog, supra.

In a preferred embodiment, the compounds have a structure depicted below in Structure 1, which depicts a nitrobenzyl photocleavable group, although as will be appreciated by those in the art, a wide variety of other moieties may be used:

Structure 1

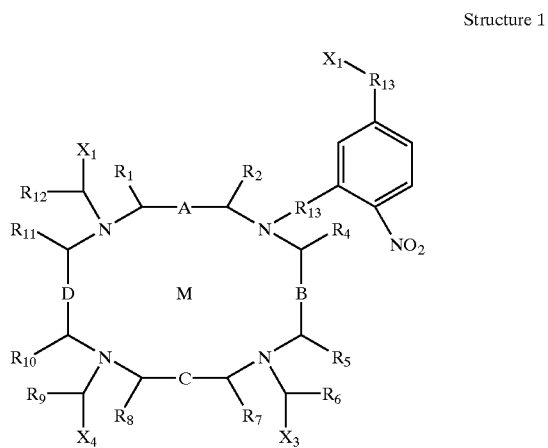

Structure 1 depicts a DOTA-type chelator, although as will be appreciated by those in the art, other chelators may be used as well. $R_{13}$ is a linker as defined below. Similarly, the $X_2$ group may be as defined above, although additional structures may be used, for example a coordination site barrier as outlined herein. Similarly, there may be substitutent groups on the aromatic ring, as is known in the art.

The blocking moiety itself may block or occupy at least one coordination site of the metal ion. That is, one or more atoms of the blocking moiety (i.e. the enzyme substrate, ligand, moiety which interacts with a physiological agent, photocleavable moiety, etc.) itself serves as a coordination atom, or otherwise blocks access to the metal ion by steric hinderance. For example, peptide based blocking moieties for protease targets may contribute coordination atoms.

In an alternative embodiment, the blocking moiety further comprises a "coordination site barrier" which is covalently tethered to the complex in such a manner as to allow disassociation upon interaction with a target substance. For example, it may be tethered by one or more enzyme substrate blocking moieties. In this embodiment, the coordination site barrier blocks or occupies at least one of the coordination sites of the metal ion in the absence of the target enzyme substance. Coordination site barriers are used when coordination atoms are not provided by the functional portion of the blocking moiety, i.e. the component of the blocking moiety which interacts with the target substance. The blocking moiety or moieties such as an enzyme substrate serves as the tether, covalently linking the coordination site barrier to the metal ion complex. In the presence of the enzyme target, the enzyme cleaves one or more of the enzyme substrates, either within the substrate or at the point of attachment to the metal ion complex, thus freeing the coordination site barrier. The coordination site or sites are no longer blocked and the bulk water is free to rapidly exchange at the coordination site of the metal ion, thus enhancing the image. As will be appreciated by those in the art, a similar result can be accomplished with other types of blocking moieties.

In one embodiment, the coordination site barrier is attached to the metal ion complex at one end, as is depicted in FIG. 3. When the enzyme target cleaves the substrate blocking moiety, the coordination site barrier is released. In another embodiment, the coordination site barrier is attached to the metal ion complex with more than one substrate blocking moiety, as is depicted in FIG. 4 for two attachments. The enzyme target may cleave only one side, thus removing the coordination site barrier and allowing the exchange of water at the coordination site, but leaving the coordination site barrier attached to the metal ion complex. Alternatively, the enzyme may cleave the coordination site barrier completely from the metal ion complex.

In a preferred embodiment, the coordination site barrier occupies at least one of the coordination sites of the metal ion. That is, the coordination site barrier contains at least one atom which serves as at least one coordination atom for the metal ion. In this embodiment, the coordination site barrier may be a heteroalkyl group, such as an alkyl amine group, as defined above, including alkyl pyridine, alkyl pyrroline, alkyl pyrrolidine, and alkyl pyrole, or a carboxylic or carbonyl group. The portion of the coordination site barrier which does not contribute the coordination atom may also be consider a linker group. Preferred coordination site barriers are depicted in FIGS. 3 and 4.

In an alternative embodiment, the coordination site barrier does not directly occupy a coordination site, but instead blocks the site sterically. In this embodiment, the coordination site barrier may be an alkyl or substituted group, as defined above, or other groups such as peptides, proteins, nucleic acids, etc.

In this embodiment, the coordination site barrier is preferably linked via two enzyme substrates to opposite sides of the metal ion complex, effectively "stretching" the coordination site barrier over the coordination site or sites of the metal ion complex, as is depicted in FIGS. 1 and 4.

In some embodiments, the coordination site barrier may be "stretched" via an enzyme substrate on one side, covalently attached to the metal ion complex, and a linker moeity, as defined below, on the other. In an alternative embodiment, the coordination site barrier is linked via a single enzyme substrate on one side; that is, the affinity of the coordination site barrier for the metal ion is higher than that of water, and thus the blocking moiety, comprising the coordination site barrier and the enzyme substrate, will block or occupy the available coordination sites in the absence of the target enzyme.

In some embodiments, the metal ion complexes of the invention have a single associated or bound blocking moiety. In such embodiments, the single blocking moiety impedes the exchange of water molecules in at least one coordination site. Alternatively, as is outlined below, a single blocking moiety may hinder the exchange of water molecules in more than one coordination site, or coordination sites on different chelators.

In alternative embodiments, two or more blocking moieties are associated with a single metal ion complex, to impede the exchange of water in at least one or more coordination sites.

It should be appreciated that the blocking moieties of the present invention may further comprise a linker group as well as a functional blocking moiety. That is, blocking moieties may comprise functional blocking moieties in combination with a linker group and/or a coordination site barrier.

Linker groups (sometimes depicted herein as $R_{13}$) will be used to optimize the steric considerations of the metal ion complex. That is, in order to optimize the interaction of the blocking moiety with the metal ion, linkers may be introduced to allow the functional blocking moiety to block or occupy the coordination site. In general, the linker group is chosen to allow a degree of structural flexibility. For example, when a blocking moiety interacts with a physiological agent which does not result in the blocking moiety being cleaved from the complex, the linker must allow some movement of the blocking moiety away from the complex, such that the exchange of water at at least one coordination site is increased.

Generally, suitable linker groups include all R groups listed above (with the exception of hydrogen). Preferred groups include, but are not limited to, alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole, carbonyls, OH, COOH, glycols, etc.

The selection of the linker group is generally done using well known molecular modeling techniques, to optimize the obstruction of the coordination site or sites of the metal ion. In addition, the length of this linker may be very important in order to achieve optimal results. The length of the linker, i.e the spacer between the chelator and the coordination atom(s) of the blocking moiety, contributes to the steric conformation and association of the coordination atoms with the metal ion, thus allowing excellent blocking of the metal ion by the blocking moiety.

The blocking moiety is attached to the metal ion complex in a variety of ways. In a preferred embodiment, as noted above, the blocking moiety is attached to the metal ion complex via a linker group. Alternatively, the blocking moiety is attached directly to the metal ion complex; for example, as outlined below, the blocking moiety may be a substituent group on the chelator.

In a preferred embodiment at least one of the R groups attached to the "arms" of the chelator, for example $R_3$, $R_6$, $R_9$ or $R_{12}$ of the DOTA structures, or $R_{14}$, $R_{15}$, $R_{18}$, $R_{21}$ or $R_{22}$ of the DTPA structures, comprises an alkyl (including substituted and heteroalkyl groups), or aryl (including substituted and heteroaryl groups), i.e. is a group sterically bulkier than hydrogen. This is particular useful to drive the equilibrium towards "locking" the coordination atom of the arm into place to prevent water exchange, as is known for standard MRI contrast agents. Preferred groups include the C1 through C6 alkyl groups with methyl being particularly preferred, including heteroatoms.

This is particularly preferred when the blocking moiety is attached via one of the "arms", for example when a blocking moiety is at position $X_1$ to $X_4$ (Structure 2) or position $X_5$ to $X_9$ (Structure 7).

However the inclusion of too many groups may drive the equilibrium in the other direction effectively locking the coordination atom out of position. Therefore in a preferred embodiment only 1 or 2 of these positions is a non-hydrogen group, unless other methods are used to drive the equilibrium towards binding.

The blocking moieties are chosen and designed using a variety of parameters. In the embodiment which uses a coordination site barrier, i.e. when the functional group of the blocking moiety does not provide a coordination atom, and the coordination site barrier is fastened or secured on two sides, the affinity of the coordination site barrier of the blocking moiety for the metal ion complex need not be great, since it is tethered in place. That is, in this embodiment, the complex is "off" in the absence of the target substance. However, in the embodiment where the blocking moiety is linked to the complex in such a manner as to allow some rotation or flexibility of the blocking moiety, for example, it is linked on one side only, such as the galactose embodiment of the examples, the blocking moiety should be designed such that it occupies the coordination site a majority of the time. As described herein, these agents may be "locked" off using R groups on the carboxylic acid "arms" of a chelator, to reduce the rotational freedom of the group and thus effectively drive the equilibrium to the "off" position, and thus result in a larger percentage increase in the signal in the presence of the target.

When the blocking moiety is not covalently tethered on two sides, as is depicted in FIGS. 1 and 4, it should be understood that blocking moieties and coordination site barriers are chosen to maximize three basic interactions that allow the blocking moiety to be sufficiently associated with the complex to hinder the rapid exchange of water in at least one coordination site of the complex. First, there may be electrostatic interactions between the blocking moiety and the metal ion, to allow the blocking moiety to associate with the complex. Secondly, there may be Van der Waals and dipole-dipole interactions. Thirdly, there may be ligand interactions, that is, one or more functionalities of the blocking moiety may serve as coordination atoms for the metal. In addition, linker groups may be chosen to force or favor certain conformations, to drive the equilibrium towards an associated blocking moiety. Similarly, removing degrees of freedom in the molecule may force a particular conformation to prevail. Thus, for example, the addition of alkyl groups, and particularly methyl groups, at "arm" positions when the blocking moiety is attached at the arm position can lead the blocking moiety to favor the blocking position. Similar restrictions can be made in the other embodiments, as will be appreciated by those in the art.

Furthermore, effective "tethering" of the blocking moiety down over the metal ion may also be done by engineering in other non-covalent interactions that will serve to increase the affinity of the blocking moiety to the chelator complex, as is depicted below.

Potential blocking moieties may be easily tested to see if they are functional; that is, if they sufficiently occupy or block the appropriate coordination site or sites of the complex to prevent rapid exchange of water. Thus, for example, complexes are made with potential blocking moieties and then compared with the chelator without the blocking moiety in imaging experiments. Once it is shown that the blocking moiety is a sufficient "blocker", the target substance is added and the experiments repeated, to show that interaction with the target substance increases the exchange of water and thus enhances the image.

In addition to the blocking moieties outlined herein, the compositions of the invention have at least one targeting moiety. That is, a targeting moiety may be attached at any of the R positions (or to a linker, including a polymer, or to a blocking moiety, etc., as is more fully described below). In some embodiments, the targeting moiety replaces a coordination atom, although this is not generally preferred in clinical applications, as this may increase toxicity. By "targeting moiety" herein is meant a functional group which serves to target or direct the complex to a particular location, cell type, diseased tissue, or association. In general, the targeting moiety is directed against a target molecule. As will be appreciated by those in the art, the MRI contrast agents of the invention are generally injected intravenously; thus preferred targeting moieties are those that allow concentration of the agents in a particular localization. In a preferred embodiment, the agent is partitioned to the location in a non-1:1 ration. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In a preferred embodiment, the targeting moiety allows targeting of the MRI agents of the invention to a particular tissue or the surface of a cell. That is, in a preferred embodiment the MRI agents of the invention need not be taken up into the cytoplasm of a cell to be activated.

In a preferred embodiment, the targeting moiety is a peptide. For example, chemotactic peptides have been used to image tissue injury and inflammation, particularly by bacterial infection; see WO 97/14443, hereby expressly incorporated by reference in its entirety.

In a preferred embodiment, the targeting moiety is an antibody. The term "antibody" includes antibody fragments, as are known in the art, including Fab $Fab_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522–525 (1986); Riechmann et al., Nature 332:323–329 (1988); and Presta, Curr. Op. Struct. Biol. 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature 321:522–525 (1986); Riechmann et al., Nature 332:323–327 (1988); Verhoeyen et al., Science 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779–783 (1992); Lonberg et al., Nature 368:856–859 (1994); Morrison, Nature 368:812–13 (1994); Fishwild et al., Nature Biotechnology 14:845–51 (1996); Neuberger, Nature Biotechnology, 14:826 (1996); Lonberg and Huszar, Intern. Rev. Immunol. 13:65–93 (1995).

Bispecific antibodies are monoclonal, preferably human or humanized, antibodies that have binding specificities for at least two different antigens. In the present case, one of the binding specificities is for a first target molecule and the other one is for a second target molecule.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J. 10:3655–3659 (1991)

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells, including, but not limited to, HER2.

In addition, antibodies against physiologically relevant carbohydrates may be used, including, but not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In one embodiment, antibodies against virus or bacteria can be used as targeting moieties. As will be appreciated by those in the art, antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including Bacillus; Vibrio, e.g. *V. cholerae;* Escherichia, e.g. Enterotoxigenic *E. coli,* Shigella, e.g. *S. dysenteriae;* Salmonella, e.g. *S. typhi;* Mycobacterium e.g. *M. tuberculosis, M. leprae;* Clostridium, e.g. *C. botulinum, C. tetani, C. difficile, C.perfringens;* Cornyebacterium, e.g. *C. diphtheriae;* Streptococcus, *S. pyogenes, S. pneumoniae;* Staphylococcus, e.g. *S. aureus;* Haemophilus, e.g. *H. influenzae;* Neisseria, e.g. *N. meningitidis, N. gonorrhoeae;* Yersinia, e.g. *G. lamblia Y. pestis,* Pseudomonas, e.g. *P. aeruginosa, P. putida;* Chlamydia, e.g. *C. trachomatis;* Bordetella, e.g. *B. pertussis;* Treponema, e.g. *T palladium;* and the like) may be used.

In a preferred embodiment, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In a preferred embodiment, the targeting moiety is a carbohydrate. By "carbohydrate" herein is meant a compound with the general formula $Cx(H2O)y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, man nose, fucose, galactosamine, (particularly N-acetylglucosamine), glucosamine, glucose and sialic acid, and in particular the glycosylation component that allows binding to certain receptors such as cell surface receptors.

Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety.

In addition, the use of carbohydrate targeting moieties can allow differential uptake into different tissues or altered half-life of the compound.

In a preferred embodiment, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In addition, as will be appreciated by those in the art, any moiety which may be utilized as a blocking moiety can be used as a targeting moiety. Particularly preferred in this regard are enzyme inhibitors, as they will not be cleaved off and will serve to localize the MRI agent in the location of the enzyme.

In a preferred embodiment, the targeting moiety may be used to either allow the internalization of the MRI agent to the cell cytoplasm or localize it to a particular cellular compartment, such as the nucleus.

In a preferred embodiment, the targeting moiety is all or a portion of the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); Baldin et al., EMBO J. 9:1511 (1990); Watson et al., Biochem. Pharmcol. 58:1521 (1999), all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499–509; the human retinoic acid receptor-β nuclear localization signal (ARRRRP); NFκB p50 (EEVQRKRQKL; Ghosh et al., Cell 62:1019 (1990); NFκB p65 (EEKRKRTYE; Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, targeting moieties for the hepatobiliary system are used; see U.S. Pat. Nos. 5,573,752 and 5,582,814, both of which are hereby incorporated by reference in their entirety.

Thus, as outlined herein, the MRI agents of the invention comprise a paramagnetic metal ion bound to a chelator, at least one blocking moiety and at least one targeting moiety. In a preferred embodiment, the metal ion complexes of the invention have the formula shown in Structure 2:

Structure 2

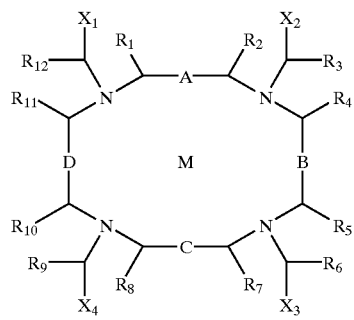

In Structure 2, M is a paramagnetic metal ion selected from the group consisting of Gd(III), Fe(III), Mn(II), Yt(III), and Dy(III). A, B, C and D are each either single or double bonds, with single bonds being preferred. The $R_1$ through $R_{12}$ groups are substitution groups, including hydrogen, alkyl groups including substituted alkyl groups and heteroalkyl groups as defined below, aryl groups including substituted aryl and heteroaryl groups as defined below, sulfur moieties, amine groups, oxo groups carbonyl groups, halogens, nitro groups, imino groups, alcohol groups, alkyoxy groups, amido groups, phosphorus moieties, ethylene glycols, ketones, aldehydes, esters, ethers, blocking moieties and targeting moieties as described above. $X_1$ through $X_4$ are —OH, —COO—, —(CH2)$_n$OH (with —CH$_2$OH being preferred), —(CH2)$_n$COO— (with CH$_2$COO— being preferred), a blocking moiety or a targeting moiety. n is from 1 to 10, with from 1 to 5 being preferred. At least one of $R_1$ to $R_{12}$ and $X_1$ to $X_4$ is a blocking moiety, and at least one of $R_1$ to $R_{12}$ and $X_1$ to $X_4$ (different from the blocking moiety) is a targeting moiety.

Preferred DOTA embodiments of the invention are depicted below in Structures 3 to 6. These structures are depicted without R groups, although assuming A, B, C and D are single bonds, there are two hydrogens attached to each carbon.

Structure 3

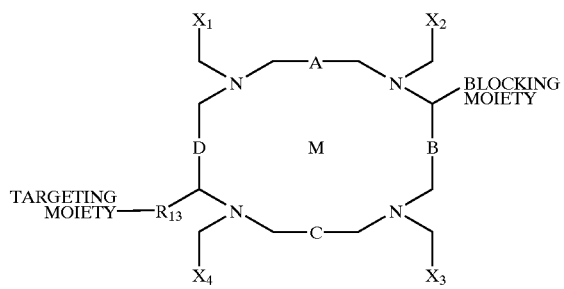

Structure 3 depicts a DOTA derivative with the blocking moiety and the targeting moiety attached to the carbons of the macrocycle and on "opposite" sides of the molecule. $R_{13}$ is an optional linker, described herein. As will be appreciated by those in the art, these moieties may be attached to any two carbon atoms of the macrocycle.

Structure 4

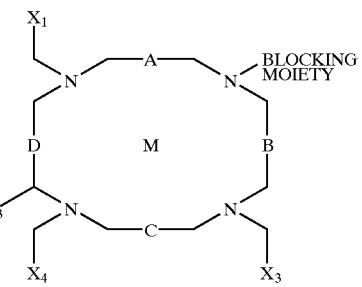

Structure 4 depicts the blocking moiety as replacing one of the carboxylic "arms" and a targeting moiety, again with an optional $R_{13}$ linker, on the opposite side of the molecule. Again, any combination of "arm" and macrocycle carbon may be used, as will be appreciated by those in the art.

Structure 5

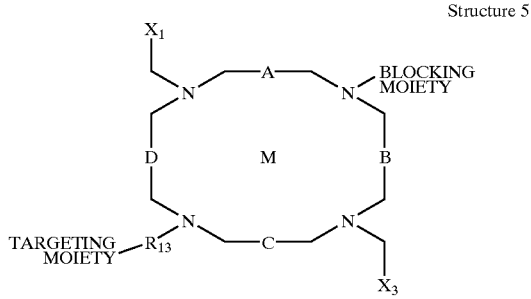

Structure 5 depicts both the blocking moiety and the targeting moiety joined to "arms" of the macrocycle. Again, any two "arms" may be used.

Structure 6

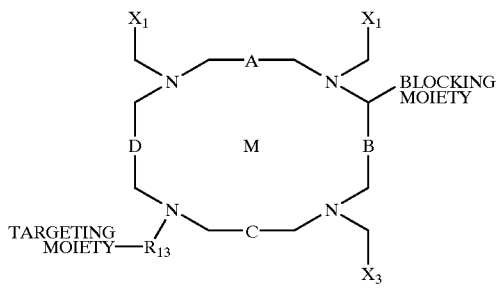

Structure 6 depicts the targeting moiety replacing an arm of the macrocycle and the blocking moiety on a carbon of the macrocycle. Again, any two positions may be used.

As applied to DOTA, a preferred embodiment utilizes the four nitrogens of the DOTA ring, and the $X_1$–$X_4$ groups to provide 8 of the coordination atoms for the paramagnetic metal ion. The ninth coordination atom is provided by a blocking moiety which is substituted at one of the $R_1$ to $R_{12}$ positions. A targeting moiety is present at a different $R_1$ to $R_{12}$ position. In a preferred embodiment, the other R groups are either hydrogen or methyl; in a particularly preferred embodiment the chelator is Gd-MCTA, which has a single methyl group on the DOTA ring (see Meyer et al., Invest. Radiol. 25:S53 (1990)).

An additional preferred embodiment utilizes the four nitrogens of the DOTA ring, and three of the X groups to provide 7 of the coordination atoms for the paramagnetic metal ion. The remaining coordination atoms are provided by a blocking moiety which is substituted at the remaining X position. Alternatively, the coordination sites are either filled by coordination atoms provided by the X groups, or blocked by the X group structure, or both. In addition, some of the structures herein do not depict the A, B, C and D bonds, but as for the other embodiments, these bonds may be either single or double bonds.

In the DOTA-structures depicted herein, any or all of A, B, C or D may be a single bond or a double bond. It is to be understood that when one or more of these bonds are double bonds, there may be only a single substitutent group attached to the carbons of the double bond. For example, when A is a double bond, there may be only a single $R_1$ and a single $R_2$ group attached to the respective carbons; in a preferred embodiment, as described below, the $R_1$ and $R_2$ groups are hydrogen. In a preferred embodiment, A is a single bond, and it is possible to have two $R_1$ groups and two $R_2$ groups on the respective carbons. In a preferred embodiment, these groups are all hydrogen with the exception of a single blocking moiety and a single targeting moiety, but alternate embodiments utilize two R groups which may be the same or different. That is, there may be a hydrogen and a blocking group attached in the $R_1$ position, and two hydrogens, two alkyl groups, or a hydrogen and an alkyl group in the $R_2$ positions, etc.

It is to be understood that the exact composition of the $X_1$–$X_4$ (Structure 2) or $X_5$–$X_9$ (Structure 7) groups will depend on the presence of the metal ion. That is, in the absence of the metal ion, the groups may be —OH, —COOH, —(CH$_2$)$_n$OH, or (CH$_2$)$_n$COOH; however, when the metal is present, the groups may be —OH, —COO—, —(CH$_2$)$_n$O—, or (CH$_2$)$_n$COO—.

In preferred embodiments, there is a single blocking moiety and a single targeting moiety attached to the metal ion complex. That is, all but two of the R groups are hydrogen. It should be appreciated that the blocking moiety and targeting moiety may be at any of the R positions.

Preferred DTPA embodiments of the invention are depicted below in Structures 7 to 11. These structures are depicted without non-hydrogen R groups, although in preferred embodiments there are two hydrogens attached to each carbon. In addition, as for the DOTA structures, a variety of different combinations of sites can be used; two arms, an arm and a carbon of the chelate, etc.

Structure 7

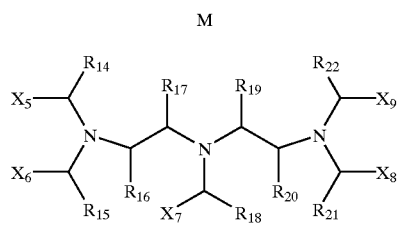

In Structure 7, M is a paramagnetic metal ion selected from the group consisting of Gd(III), Fe(III), Mn(II), Yt(III), and Dy(III). A, B, C and D are each either single or double bonds. The $R_{14}$ through $R_{22}$ groups are substitution groups, including hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, blocking moieties and targeting moieties as described above. $X_5$ through $X_9$ are —OH, —COO—, —(CH2)$_n$OH (with —CH$_2$OH being preferred), —(CH2)$_n$COO— (with CH$_2$COO— being preferred), a blocking moiety or a targeting moiety. n is from 1 to 10, with from 1 to 5 being preferred. At least one of $R_{14}$ to $R_{22}$ and $X_5$ to $X_9$ is a blocking moiety and at least one of $R_{14}$ to $R_{22}$ and $X_5$ to $X_9$ (different from the blocking moiety) is a targeting moiety.

Structure 8

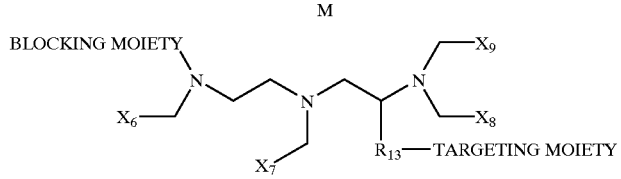

Structure 9

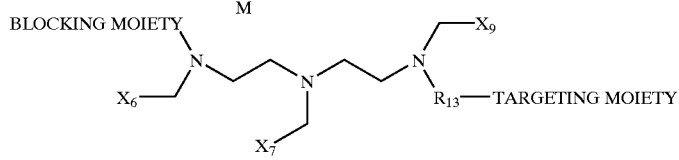

Structure 10

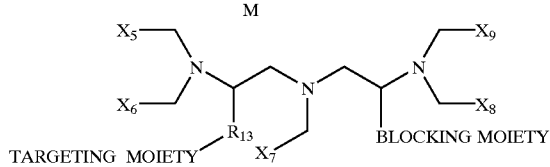

Structure 11

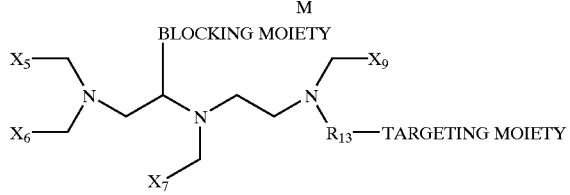

In another embodiment, the metal ion complexes have the formula depicted in Structure 12:

Structure 12:

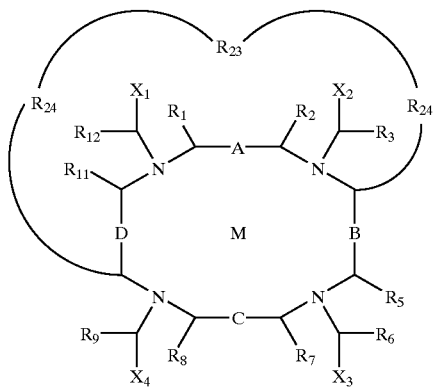

In this embodiment, $R_{23}$ and $R_{24}$ comprise a blocking moiety, with $R_{23}$ being a coordination site barrier which also serves to contribute a coordination atom. It is to be understood that the $R_{24}$ groups may be attached at any of the $R_1$ to $R_{12}$ positions, or to $X_1$–$X_4$ positions. Preferred $R_{23}$ groups include, but are not limited to, compounds listed above that provide a coordination atom, blocking moieties, and those shown in the Figures. The $R_{24}$ groups may also comprise a linker, as defined above (generally as $R_{13}$) and as shown in Structure 13, below. At least one of the $R_1$–$R_{12}$ and $X_1$–$X_4$ groups comprises a targeting moiety (not shown). Preferred $R_{24}$ groups include enzyme substrates which are cleaved upon exposure to the enzyme, such as carbohydrates and peptides. Accordingly, when the target substance is a carbohydrase such as β-galactosidase, the compositions have the formula shown in FIG. 1.

In place of the carbohydrates in FIG. 1, an alternative embodiment utilizes peptides. That is, a peptide comprising 2 to 5 amino acids or analogs may be "stretched" from one side of the complex to the other, and linker groups may or may not be used. Similarly, nucleic acids may be used.

Alternatively, there may not be covalent attachment at both ends. As discussed above, effective "tethering" of the blocking moiety down over the metal ion may also be done by engineering in other non-covalent interactions that will serve to increase the affinity of the blocking moiety to the chelator complex. Thus, for example, electrostatic interactions may be used, as is generally depicted below for a DOTA derivative in FIG. 2.

As will be appreciated by those in the art, the MRI compositions of the invention may take on a wide variety of different conformations, as outlined herein. In a preferred embodiment, the MRI agents are "monomers" as depicted in the Structures. Alternatively, in a preferred embodiment, the MRI contrast agents of the invention comprise more than one metal ion, such that the signal is increased. As is outlined below, this may be done in a number of ways. FIG. 6 generally depicts a variety of different configurations of the present invention.

In a preferred embodiment, the MRI agents of the invention comprise at least two paramagnetic metal ions, each with a chelator and blocking moiety; that is, multimeric MRI agents are made. In a preferred embodiment, the chelators are linked together, either directly or through the use of a linker such as a coupling moiety or polymer. For example, using substitution groups that serve as functional groups for chemical attachment on the chelator, attachment to other chelators may be accomplished. As will be appreciated by those in the art, attachment of more than one MRI agent may also be done via the blocking moieties (or coordination site barriers, etc.), although these are generally not preferred.

In one embodiment, the chelators are linked together directly, using at least one functional group on each chelator. In this embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

This may be accomplished using any number of stable bifunctional groups well known in the art, including homobifunctional and heterobifunctional linkers (see Pierce Catalog and Handbook, 1994, pages T155–T200, hereby expressly incorporated by reference). This may result in direct linkage, for example when one chelator comprises a primary amine as a functional group and the second comprises a carboxy group as the functional group, and carbodiimide is used as an agent to activate the carboxy for attach by the nucleophilic amine (see Torchilin et al., *Critical Rev. Therapeutic Drug Carrier Systems*, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. As will be appreciated by those in the art, these MRI contrast agents may be monomeric (i.e. one metal ion, one chelator, one blocking moiety) or a duplex or dimer, as is generally described below (i.e. two metal ions, two chelators, one blocking moiety). The targeting moieties can be added to the individual monomers, individual dimers (or multimers), or to the polymer. Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used. A preferred polymer comprising a poly(alkylene oxide is also described in U.S. Pat. No. 5,817,292, incorporated by reference.

A preferred polymer is polylysine, as the —$NH_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred. In addition, polymers of chelates with a mean molecular weight of between 10–40 kDA serve to distinguish between malignant and benign tumors; see WO 96/35456, hereby incorporated by reference in its entirety.

It should be understood that the multimeric MRI agents of the invention may be made in a variety of ways, including those listed above. What is important is that manner of attachment does not significantly alter the functionality of the agents; that is, the agents must still be "off" in the absence of the target substance and "on" in its presence.

In addition, as will be appreciated by those in the art, when multimeric (all the same monomers) or oligomeric (different monomers)compositions are made, the multimer or oligomer may have one or more targeting moieties. That is, each chelate may comprise a targeting moiety, or a single oligomer, comprising a plurality of chelates, can have a single targeting moiety; alternatively, less than 1 per chelate may be used but more than 1 per oligomer.

In a preferred embodiment, the MRI contrast agents of the invention are "duplexes". In this embodiment, the MRI duplex comprises two chelators, each with a paramagnetic metal ion, and at least one blocking moiety that restricts the exchange of water in at least one coordination site of each chelator. In this way, a sort of signal amplification occurs, with two metal ions increasing the signal with a single target molecule. While "duplex" implies two chelators, it is intended to refer to complexes comprising a single blocking moiety donating coordination atoms to more than 1 metal ion/chelator complex. As will be appreciated by those in the art, the MRI agents of this embodiment may have a number of different conformations, as is generally shown in FIG. 6. As will be appreciated by those in the art, the $R_{26}$, $R_{27}$ and $R_{28}$ groups of the figure can be attached to any of the positions described herein.

As outlined above, the MRI duplex moieties may also be combined into higher oligomers, either by direct linkage or via attachment to a polymer.

In a preferred duplex embodiment, the blocking moiety is BAPTA, as is generally depicted in FIGS. 5 and 7, with propyl linking groups between the chelators and the BAPTA derivative.

In this embodiment, the blocking moiety comprises linkers and the BAPTA molecule, although any of the fura-type $Ca^{+2}$ ligands may be substituted. Without being bound by theory, it appears that one of the carboxy groups of the BAPTA moiety serves to provide a coordination atom in the absence of Ca+2. However, in the presence of Ca+2, the carboxy group chelates Ca+2, and thus is unavailable as a coordination group, thus allowing the rapid exchange of water. Preferably, the metal ion is Gd(III), the R groups are all hydrogen, and the X groups are carboxy.

In one embodiment the carboxylic acid groups of the BAPTA molecule may be protected with acetate protecting groups, resulting a neutral molecule that may then cross membranes. Once inside a cell, intracellular esterases can cleave off the acetate protecting groups, allowing the detection of $Ca^{+2}$. See Li et al., Tetrahedron 53(35):12017–12040 (1997).

As will be appreciated by those in the art, the structure depicted in FIGS. 5 and 7 may be altered, for example, replacing the phenyl groups of the BAPTA derivative with cycloalkyl groups, or removing them entirely, as is generally depicted in FIG. 7.

As noted above, the carboxylic acids of the BAPTA molecule may also be protected using acetate protecting groups, to render a neutral molecule for entry into cells, that then can be reactivated via cleavage by intracellular esterases.

In addition, although FIGS. 5 and 7 have ethylene groups between the oxygens of the bridge of BAPTA, methylene and propylene may also be used, as well as substituted derivatives of these.

In a preferred embodiment, A, B, C and D are single bonds, $R_1$–$R_{12}$ are hydrogen, and each $R_{13}$ is —$CH_2O$—, with the $CH_2$ group being attached to the macrocycle.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992)).

For DOTA derivatives, the synthesis depends on whether nitrogen substitution or carbon substitution of the cyclen ring backbone is desired. For nitrogen substitution, such as is exemplified by the galactose-DOTA structures of the examples, the synthesis begins with cyclen or cyclen derivatives, as is well known in the art; see for example U.S. Pat. Nos. 4,885,363 and 5,358,704. FIGS. 3 and 4 depict the nitrogen substitution as exemplified by galactose-DOTA derivatives.

For carbon substitution, such as is exemplified by the BAPTA-DOTA structures of the examples, well known techniques are used. See for example Moi et al., supra, and Gansow, supra. FIGS. 5 and 7 depict the carbon substitution as exemplified by the BAPTA-DOTA type derivatives.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

Once made, the compositions of the invention find use in a variety of applications. In particular, the metal ion complexes of the invention have use as magnetic resonance imaging contrast or enhancement agents. Specifically, the functional MRI agents of the invention have several important uses. First, they may be used to diagnose disease states of the brain, as is outlined below. Second, they may be used in real-time detection and differentiation of myocardial infraction versus ischemia. Third, they may be used in in vivo, i.e. whole organism, investigation of antigens and immunocytochemistry. for the location of tumors. Fourth, they may be used in the identification and localization of toxin and drug binding sites. In addition, they may be used to perform rapid screens of the physiological response to drug therapy.

The metal ion complexes of the invention may be used in a similar manner to the known gadolinium MRI agents. See for example, Meyer et al., supra; U.S. Pat. Nos. 5,155,215; 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

The administration of the agents of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise an MRI agent in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In addition, in one embodiment, the MRI agents are added in a micellular formulation; see U.S. Pat. No. 5,833,948, hereby incorporated by reference.

Combinations of the compositions may be administered. Moreover, the compositions may be administered in combination with other therapeutics or imaging agents.

Generally, sterile aqueous solutions of the contrast agent complexes of the invention are administered to a patient in a variety of ways, including orally, intrathecally and especially intraveneously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers, including polyethylene glycol, to the chelator (see U.S. Pat. Nos. 5,155,215 and 5,605,672). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier with blocking moieties which detect Ca+2 ions. These compounds are used in MRI of a variety of neurological disorders, including Alzeheimer's disease. Currently it is difficult to correctly diagnosis Alzeheimer's disease, and it would be useful to be able to have a physiological basis to distinguish Alzeheimer's disease from depression, or other treatable clinical symptoms for example.

The examples outlined herein serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are expressly incorporated by reference.

We claim:

1. An MRI agent composition comprising:
    a) a first Gd(III) ion bound to a first chelator such that said first Gd(III) ion has coordination atoms in at least 7 coordination sites of said first Gd(III) ion;
    b) a first blocking moiety covalently attached to said first chelator which hinders the rapid exchange of water in the remaining coordination sites of said first Gd(III) ion; and
    c) at least a first targeting moiety;
    wherein said first blocking moiety is attached such that interaction of said first blocking moiety with a target substance increases the exchange of water in the remaining coordination sites of said first Gd(III) ion.

2. An MRI agent composition according to claim 1 further comprising:
    a) a second Gd(III) ion bound to a second chelator such that said second Gd(III) ion has coordination atoms in at least 7 coordination sites of said second Gd(III) ion;
    b) a second blocking moiety covalently attached to said second chelator which hinders the rapid exchange of water in the remaining coordination sites of said second Gd(III) ion;
    wherein said first targeting moiety is covalently attached to said first chelator, wherein said second blocking moiety is attached such that interaction of said second blocking moiety with a target substance increases the exchange of water in the remaining coordination sites of said second Gd(III) ion and wherein said first and second chelators are covalently attached.

3. An MRI agent composition according to claim 2 wherein said covalent attachment utilizes a linker.

4. An MRI agent composition according to claim 1 further comprising a second Gd(III) ion bound to a second chelator such that said second Gd(III) ion has coordination atoms in at least 7 coordination sites of said second Gd(III) ion, wherein said first targeting moiety is covalently attached to said first chelator, wherein said first blocking moiety is attached such that interaction of said first blocking moiety with a target substance increases the exchange of water in the remaining coordination sites of said first and second Gd(III) ions and wherein said first and second chelators are covalently attached.

5. An MRI agent composition according to claim 2 wherein said covalent attachment utilizes a linker.

6. An MRI agent composition according to claim 1 further comprising:
    a) a second Gd(III) ion bound to a second chelator such that said second Gd(III) ion has coordination atoms in at least 7 coordination sites of said second Gd(III) ion;
    b) a second blocking moiety covalently attached to said second chelator which hinders the rapid exchange of water in the remaining coordination sites of said second Gd(III) ion; and
    c) a second targeting moiety, covalently attached to said second chelator;
    wherein said first targeting moiety is covalently attached to said first chelator, wherein said second blocking moiety is attached such that interaction of said second blocking moiety with a target substance increases the exchange of water in the remaining coordination sites of said second Gd(III) ion and wherein said first and second chelators are covalently attached.

7. An MRI agent composition according to claim 6 wherein said covalent attachment utilizes a linker.

8. An MRI agent composition according to claim 1 further comprising a second Gd(III) ion bound to a second chelator such that said second Gd(III) ion has coordination atoms in at least 7 coordination sites of said second Gd(III) ion, wherein said first targeting moiety is covalently attached to said first chelator, wherein said second chelator comprises a covalently attached second targeting moiety, wherein said first blocking moiety is attached such that interaction of said first blocking moiety with a target substance increases the exchange of water in the remaining coordination sites of said first and second Gd(III) ions and wherein said first and second chelators are covalently attached.

9. An MRI agent composition according to claim 8 wherein said covalent attachment utilizes a linker.

10. An MRI agent composition according to claim 1 further comprising:
 a) a second Gd(III) ion bound to a second chelator such that said second Gd(III) ion has coordination atoms in at least 7 coordination sites of said second Gd(III) ion;
 b) a second blocking moiety covalently attached to said second chelator which hinders the rapid exchange of water in the remaining coordination sites of said second Gd(III) ion; and
 c) a polymer;
wherein said second blocking moiety is attached such that interaction of said second blocking moiety with a target substance increases the exchange of water in the remaining coordination sites of said second Gd(III) ion, wherein said first and second chelators are covalently attached to said polymer, and wherein said first targeting moiety is covalently attached to said polymer.

11. An MRI agent composition according to claim 1 further comprising:
 a) a second Gd(III) ion bound to a second chelator such that said second Gd(III) ion has coordination atoms in at least 7 coordination sites of said second Gd(III) ion;
 b) a second blocking moiety covalently attached to said second chelator which hinders the rapid exchange of water in the remaining coordination sites of said second Gd(III) ion;
 c) a second targeting moiety, covalently attached to said second chelator; and
 d) a polymer;
wherein said second blocking moiety is attached such that interaction of said second blocking moiety with a target substance increases the exchange of water in the remaining coordination sites of said second Gd(III) ion and wherein said first and second chelators are covalently attached to said polymer.

12. An MRI agent composition according to claim 1 wherein said first Gd(III) ion has coordination atoms in 8 coordination sites of said first Gd(III) ion.

13. An MRI agent composition according to claim 1 wherein said first chelator is DOTA or substituted DOTA.

14. An MRI agent composition according to claim 1 wherein said first chelator is DTPA or substituted DTPA.

15. A pharmaceutical composition comprising an MRI agent composition according to claim 1 and a pharmaceutically acceptable carrier.

16. A method of magnetic resonance imaging of a cell, tissue or patient comprising administering an MRI agent composition according to claim 1 to a cell, tissue or patient and rendering a magnetic resonance image of said cell, tissue or patient.

17. An MRI agent composition according to claim 1 having the formula:

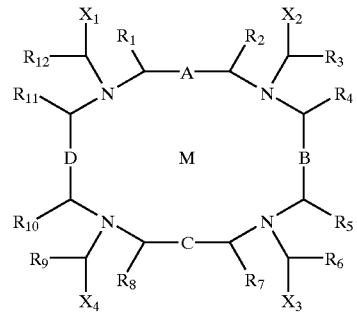

wherein
 M is a paramagnetic ion comprising said first Gd(III) ion;
 A, B, C and D are selected from the group consisting of single bonds and double bonds;
 $X_1$, $X_2$, $X_3$ and $X_4$ are —OH, —COO—, —CH$_2$OH—CH$_2$COO—, said first blocking moiety or said first targeting moiety;
 $R_1$–$R_{12}$ are each a substitution group;
 wherein at least one of $X_1$–$X_4$ and $R_1$–$R_{12}$ is said first blocking moiety and wherein at least one of $X_1$–X4 and $R_1$–$R_{12}$ is said first targeting moiety.

18. An MRI agent composition according to claim 1 having the formula:

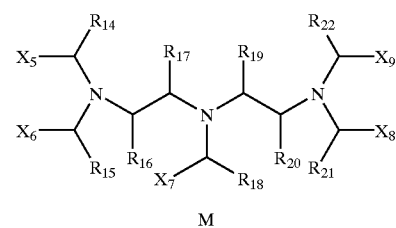

wherein
 M is a paramagnetic metal ion comprising said Gd(III) ion;
 $X_5$, $X_6$, $X_7$, $X_8$ and $X_9$ are —OH, —COO—, —CH$_2$OH—CH$_2$COO—, said first blocking moiety or said first targeting moiety;
 $R_{14}$–$R_{22}$ are each a substitution group;
 wherein at least one of $X_5$–$X_9$ and $R_{14}$–$R_{22}$ is said first blocking moiety and wherein at least one of $X_5$–$X_9$ and $R_{14}$–$R_{22}$ is said first targeting moiety.

* * * * *